US010405951B1

(12) United States Patent
Kopelman et al.

(10) Patent No.: US 10,405,951 B1
(45) Date of Patent: Sep. 10, 2019

(54) METHOD FOR MANIPULATING A DENTAL VIRTUAL MODEL, METHOD FOR CREATING PHYSICAL ENTITIES BASED ON A DENTAL VIRTUAL MODEL THUS MANIPULATED, AND DENTAL MODELS THUS CREATED

(71) Applicant: Align Technology, Inc., San Jose, CA (US)

(72) Inventors: Avi Kopelman, Palo Alto, CA (US); Eldad Taub, Reut (IL)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 16/164,092

(22) Filed: Oct. 18, 2018

Related U.S. Application Data

(63) Continuation of application No. 15/388,580, filed on Dec. 22, 2016, now Pat. No. 10,143,541, which is a
(Continued)

(51) Int. Cl.
*G06F 19/00* (2018.01)
*A61C 9/00* (2006.01)
(Continued)

(52) U.S. Cl.
CPC .............. *A61C 9/004* (2013.01); *A61C 5/77* (2017.02); *A61C 13/0004* (2013.01);
(Continued)

(58) Field of Classification Search
CPC ....... A61C 13/0004; A61C 13/34; A61C 5/77; A61C 9/004; G06F 17/50; G06F 19/00;
(Continued)

(56) References Cited

U.S. PATENT DOCUMENTS 2,467,432 A    4/1949   Kesling et al.
3,407,500 A   10/1968   Kesling et al.
(Continued)

FOREIGN PATENT DOCUMENTS

AU        3031677 A    5/1979
AU        517102 B2    7/1981
(Continued)

OTHER PUBLICATIONS

AADR. American Association for Dental Research, Summary of Activities, Mar. 20-23, 1980, Los Angeles, CA, p. 195.
(Continued)

*Primary Examiner* — Kidest Bahta
(74) *Attorney, Agent, or Firm* — Wilson Sonsini Goodrich & Rosati

(57) ABSTRACT

A 3D virtual model of an intra oral cavity in which at least a part of a finish line of a preparation is obscured is manipulated in virtual space by means of a computer or the like to create, recreate or reconstruct finish line data and other geometrical corresponding to the obscured part. Trimmed virtual models, and trimmed physical models, can then be created utilizing data thus created. The virtual models and/or the physical models may be used in the design and manufacture of copings or of prostheses.

20 Claims, 8 Drawing Sheets

Related U.S. Application Data continuation of application No. 14/882,312, filed on Oct. 13, 2015, now Pat. No. 9,549,794, which is a continuation of application No. 14/324,784, filed on Jul. 7, 2014, now Pat. No. 9,186,228, which is a continuation of application No. 13/716,008, filed on Dec. 14, 2012, now Pat. No. 8,805,563, which is a continuation of application No. 13/227,435, filed on Sep. 7, 2011, now Pat. No. 8,359,115, which is a continuation of application No. 12/654,762, filed on Dec. 31, 2009, now Pat. No. 8,041,439, which is a continuation of application No. 12/222,287, filed on Aug. 6, 2008, now Pat. No. 7,734,368, which is a continuation of application No. 11/349,124, filed on Feb. 8, 2006, now Pat. No. 7,555,403.

(60) Provisional application No. 60/699,499, filed on Jul. 15, 2005.

(51) Int. Cl.
  *G16H 50/50* (2018.01)
  *A61C 13/00* (2006.01)
  *A61C 13/34* (2006.01)
  *A61C 5/77* (2017.01)
  *G06F 17/50* (2006.01)
  *G16H 30/20* (2018.01)

(52) U.S. Cl.
  CPC .............. *A61C 13/34* (2013.01); *G06F 17/50* (2013.01); *G16H 30/20* (2018.01); *G16H 50/50* (2018.01); *Y02P 90/265* (2015.11); *Y10T 29/49567* (2015.01)

(58) Field of Classification Search
  CPC ...... G06F 19/321; G16H 30/20; G16H 50/50; Y02P 90/265; Y10T 29/49567
  See application file for complete search history.

(56) References Cited

U.S. PATENT DOCUMENTS

| | | |
|---|---|---|
| 3,600,808 A | 8/1971 | Reeve et al. |
| 3,660,900 A | 5/1972 | Andrews et al. |
| 3,683,502 A | 8/1972 | Wallshein et al. |
| 3,738,005 A | 6/1973 | Cohen et al. |
| 3,860,803 A | 1/1975 | Levine et al. |
| 3,916,526 A | 11/1975 | Schudy et al. |
| 3,922,786 A | 12/1975 | Lavin et al. |
| 3,950,851 A | 4/1976 | Bergersen et al. |
| 3,983,628 A | 10/1976 | Acevedo et al. |
| 4,014,096 A | 3/1977 | Dellinger et al. |
| 4,195,046 A | 3/1980 | Kesling et al. |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut et al. |
| 4,500,294 A | 2/1985 | Lewis et al. |
| 4,504,225 A | 3/1985 | Yoshii |
| 4,505,673 A | 3/1985 | Yoshii et al. |
| 4,526,540 A | 7/1985 | Dellinger et al. |
| 4,575,330 A | 3/1986 | Hull et al. |
| 4,575,805 A | 3/1986 | Moermann et al. |
| 4,591,341 A | 5/1986 | Andrews et al. |
| 4,609,349 A | 9/1986 | Cain et al. |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling et al. |
| 4,676,747 A | 6/1987 | Kesling et al. |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz et al. |
| 4,798,534 A | 1/1989 | Breads et al. |
| 4,836,778 A | 6/1989 | Baumrind et al. |
| 4,837,732 A | 6/1989 | Brandestini et al. |
| 4,850,864 A | 7/1989 | Diamond et al. |
| 4,850,865 A | 7/1989 | Napolitano et al. |
| 4,856,991 A | 8/1989 | Breads et al. |
| 4,877,398 A | 10/1989 | Kesling et al. |
| 4,880,380 A | 11/1989 | Martz et al. |
| 4,889,238 A | 12/1989 | Batchelor et al. |
| 4,890,608 A | 1/1990 | Steer et al. |
| 4,935,635 A | 6/1990 | O'Harra et al. |
| 4,936,862 A | 6/1990 | Walker et al. |
| 4,937,928 A | 7/1990 | Van Der Zel et al. |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell et al. |
| 5,011,405 A | 4/1991 | Lemchen et al. |
| 5,017,133 A | 5/1991 | Miura et al. |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman et al. |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax et al. |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson et al. |
| 5,342,202 A | 8/1994 | Deshayes et al. |
| 5,368,478 A | 11/1994 | Andreiko et al. |
| 5,382,164 A | 1/1995 | Stern et al. |
| 5,395,238 A | 3/1995 | Andreiko et al. |
| 5,431,562 A | 7/1995 | Andreiko et al. |
| 5,440,326 A | 8/1995 | Quinn et al. |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern et al. |
| 5,562,448 A | 10/1996 | Mushabac et al. |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. et al. |
| 5,621,648 A | 4/1997 | Crump et al. |
| 5,645,420 A | 7/1997 | Bergersen et al. |
| 5,645,421 A | 7/1997 | Slootsky et al. |
| 5,655,653 A | 8/1997 | Chester et al. |
| 5,683,243 A | 11/1997 | Andreiko et al. |
| 5,692,894 A | 12/1997 | Schwartz et al. |
| 5,725,376 A | 3/1998 | Poirier et al. |
| 5,725,378 A | 3/1998 | Wang et al. |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson et al. |

(56) References Cited

U.S. PATENT DOCUMENTS

| | | | |
|---|---|---|---|
| 5,823,778 | A | 10/1998 | Schmitt et al. |
| 5,848,115 | A | 12/1998 | Little et al. |
| 5,857,853 | A | 1/1999 | Van et al. |
| 5,866,058 | A | 2/1999 | Batchelder et al. |
| 5,879,158 | A | 3/1999 | Doyle et al. |
| 5,880,961 | A | 3/1999 | Crump et al. |
| 5,880,962 | A | 3/1999 | Andersson et al. |
| 5,934,288 | A | 8/1999 | Avila et al. |
| 5,938,446 | A | 8/1999 | Andersson et al. |
| 5,957,686 | A | 9/1999 | Anthony et al. |
| 5,964,587 | A | 10/1999 | Sato et al. |
| 5,971,754 | A | 10/1999 | Sondhi et al. |
| 5,975,893 | A | 11/1999 | Chishti et al. |
| 6,015,289 | A | 1/2000 | Andreiko et al. |
| 6,044,309 | A | 3/2000 | Honda et al. |
| 6,049,743 | A | 4/2000 | Baba et al. |
| 6,062,861 | A | 5/2000 | Andersson |
| 6,068,482 | A | 5/2000 | Snow et al. |
| 6,099,314 | A | 8/2000 | Kopelman et al. |
| 6,123,544 | A | 9/2000 | Cleary et al. |
| 6,152,731 | A | 11/2000 | Jordan et al. |
| 6,174,168 | B1 | 1/2001 | Dehoff et al. |
| 6,183,248 | B1 | 2/2001 | Chishti et al. |
| 6,190,165 | B1 | 2/2001 | Andreiko et al. |
| 6,217,325 | B1 | 4/2001 | Chishti et al. |
| 6,217,334 | B1 | 4/2001 | Hultgren et al. |
| 6,244,861 | B1 | 6/2001 | Andreiko et al. |
| 6,309,215 | B1 | 10/2001 | Phan et al. |
| 6,315,553 | B1 | 11/2001 | Sachdeva et al. |
| 6,322,359 | B1 | 11/2001 | Jordan et al. |
| 6,350,120 | B1 | 2/2002 | Sachdeva et al. |
| 6,382,975 | B1 | 5/2002 | Poirier et al. |
| 6,398,548 | B1 | 6/2002 | Muhammad et al. |
| 6,402,707 | B1 | 6/2002 | Ernst et al. |
| 6,482,298 | B1 | 11/2002 | Bhatnagar et al. |
| 6,488,503 | B1 | 12/2002 | Lichkus et al. |
| 6,524,101 | B1 | 2/2003 | Phan et al. |
| 6,554,611 | B2 | 4/2003 | Shishti et al. |
| 6,572,372 | B1 | 6/2003 | Phan et al. |
| 6,594,539 | B1 | 7/2003 | Geng |
| 6,629,840 | B2 | 10/2003 | Chishti et al. |
| 6,705,863 | B2 | 3/2004 | Phan et al. |
| 6,722,880 | B2 | 4/2004 | Chishti et al. |
| 7,184,150 | B2 | 2/2007 | Quadling et al. |
| 7,555,403 | B2 | 6/2009 | Kopelman et al. |
| 7,698,068 | B2 | 4/2010 | Babayoff et al. |
| 7,734,368 | B2 | 6/2010 | Kopelman et al. |
| 8,041,439 | B2 | 10/2011 | Kopelman et al. |
| 8,359,115 | B2 | 1/2013 | Kopelman et al. |
| 8,734,149 | B2 | 5/2014 | Phan et al. |
| 8,805,563 | B2 | 8/2014 | Kopelman et al. |
| 9,186,228 | B2 | 11/2015 | Kopelman et al. |
| 9,549,794 | B2 | 1/2017 | Kopelman et al. |
| 10,143,541 | B2 | 12/2018 | Kopelman et al. |
| 2002/0006597 | A1 | 1/2002 | Andreiko et al. |
| 2002/0015934 | A1 | 2/2002 | Rubbert et al. |
| 2002/0137011 | A1 | 9/2002 | Shoher et al. |
| 2003/0009252 | A1 | 1/2003 | Pavlovskaia et al. |
| 2003/0139834 | A1 | 7/2003 | Nikolskiy et al. |
| 2003/0224311 | A1 | 12/2003 | Cronauer et al. |
| 2004/0128010 | A1 | 7/2004 | Pavlovskaia et al. |
| 2004/0158342 | A1 | 8/2004 | Wolf et al. |
| 2004/0172150 | A1 | 9/2004 | Perot et al. |
| 2005/0055118 | A1 | 3/2005 | Nikolskiy et al. |
| 2005/0177266 | A1 | 8/2005 | Kopelman et al. |
| 2005/0251281 | A1 | 11/2005 | O'Brien et al. |
| 2005/0271996 | A1 | 12/2005 | Sporbert et al. |
| 2005/0283065 | A1 | 12/2005 | Babayoff et al. |
| 2006/0001739 | A1 | 1/2006 | Babayoff |
| 2006/0122719 | A1 | 6/2006 | Kopelman et al. |
| 2006/0281041 | A1* | 12/2006 | Rubbert ............... G16H 50/50 433/24 |
| 2007/0081718 | A1 | 4/2007 | Rubbert et al. |
| 2012/0065952 | A1 | 3/2012 | Kopelman et al. |
| 2013/0204601 | A1 | 8/2013 | Kopelman et al. |
| 2015/0004565 | A1 | 1/2015 | Kopelman et al. |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| EP | 1607041 A2 | 12/2005 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |
| WO | WO-0008415 A1 | 2/2000 |
| WO | WO-0069357 A1 | 11/2000 |
| WO | WO-2004030565 A1 | 4/2004 |
| WO | WO-2004087000 A1 | 10/2004 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," IADR Abstracts, Program and Abstracts of Papers, 57th General Session, IADR Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

(56) References Cited

OTHER PUBLICATIONS

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).
Baumrind, "Integrated Three-Dimensional Craniofacial Mapping: Background, Principles, and Perspectives," Semin. in Orthod., 7(4):223-232 (Dec. 2001).
Begole et al., "A Computer System for the Analysis of Dental Casts," The Angle Orthod., 51(3):253-259 (Jul. 1981).
Bernard et al., "Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff, "Computerized Diagnostic Setups and Simulations," Angle Orthod., 40(1):28-36 (Jan. 1970).
Biggerstaff et al., "Computerized Analysis of Occlusion in the Postcanine Dentition," Am. J. Orthod., 61(3): 245-254 (Mar. 1972).
Biostar Opeation & Training Manual. Great Lakes Orthodontics, Ltd. 199 Fire Tower Drive, Tonawanda, New York. 14150-5890, 20 pages total (1990).
Blu, et al., "Linear interpolation revitalized", IEEE Trans. Image Proc., 13(5):710-719 (May 2004.
Bourke, "Coordinate System Transformation," (Jun. 1996), p. 1, retrieved from the Internet Nov. 5, 2004, URL<http://astronomy.swin.edu.au/-pbourke/prolection/coords>.
Boyd et al., "Three Dimensional Diagnosis and Orthodontic Treatment of Complex Malocclusions With the lnvisalipn Appliance," Semin. Orthod., 7(4):274-293 (Dec. 2001).
Brandestini et al., "Computer Machined Ceramic Inlays: In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone et al., Precision Adjustment of the Transpalatal Lingual Arch: Computer Arch Form In Predetermination, Am, Journal of Orthodontics, vol. 79, No. 2 (Feb. 1981), pp. 115-133.
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Cardinal Industrial Finishes, Powder Coatings information posted at<http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1 CAD/CAM: The Computer Moves Chairside," Part 2 F. Duret—A Man with a Vision,"Part 3 The Computer Gives New Vision—Literally," Part 4 Bytes 'N Bites—The Computer Moves from the Front Desk to the Operatory, Canadian Dental Journal, vol. 54 (9), pp. 661-666 (1988).
Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992).
Definition for gingiva. Dictionary.com pp. 1-3. Retrieved from the internet Nov. 5, 2004<http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the Cerec-Method, May 1991, 2 pages total.
Dentrac Corporation, Dentrac document, pp. 4-13 (1992).
Dent-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances—Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
European search report dated Jun. 15, 2015 for EP Application No. 06766123.1.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet:<http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management," J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et a/., "Computer-Based Image Analysis of Artificial Root Surface Caries," Abstracts of Papers, J. Dent. Res., 70:528 (Apr. 17-21, 1991).

(56) References Cited

OTHER PUBLICATIONS

Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.

Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).

Hoffmann, et al., "Role of Cephalometry for Planning of Jaw Orthopedics and Jaw Surgery Procedures," (Article Summary in English, article in German), Informatbnen, pp. 375-396 (Mar. 1991).

Hojjatie et al., "Three-Dimensional Finite Element Analysis of Glass-Ceramic Dental Crowns," J. Biomech., 23(11):1157-1166 (1990).

Huckins, "CAD-CAM Generated Mandibular Model Prototype from MRI Data," AAOMS, p. 96 (1999).

Important Tip About Wearing the Red White & Blue Active Clear Retainer System, Allesee Orthodontic Appliances-Pro Lab, 1 page 1998).

JCO Interviews, Craig Andreiko , DDS, MS on the Elan and Orthos Systems, JCO, pp. 459-468 (Aug. 1994).

JCO Interviews, Dr. Homer W. Phillips on Computers in Orthodontic Practice, Part 2, JCO. 1997; 1983:819-831.

Jerrold, "The Problem, Electronic Data Transmission and the Law," AJO-DO, pp. 478-479 (Apr. 1988).

Jones et al., "An Assessment of the Fit of a Parabolic Curve to Pre- and Post-Treatment Dental Arches," Br. J. Orthod., 16:85-93 (1989).

JP Faber et al., "Computerized Interactive Orthodontic Treatment Planning," Am. J. Orthod., 73(1):36-46 (Jan. 1978).

Kamada et.al., Case Reports on Tooth Positioners Using LTV Vinyl Silicone Rubber, J. Nihon University School of Dentistry (1984) 26(1): 11-29.

Kamada et.al., Construction of Tooth Positioners with LTV Vinyl Silicone Rubber and Some Case KJ Reports, J. Nihon University School of Dentistry (1982) 24(1):1-27.

Kanazawa et al., "Three-Dimensional Measurements of the Occlusal Surfaces of Upper Molars in a Dutch Population," J. Dent Res., 63(11):1298-1301 (Nov. 1984).

Kesling, Coordinating the Predetermined Pattern and Tooth Positioner with Conventional Treatment, KN Am. J. Orthod. Oral Surg. (1946) 32:285-293.

Kesling et al., The Philosophy of the Tooth Positioning Appliance, American Journal of Orthodontics and Oral surgery. 1945; 31:297-304.

Kleeman et al., the Speed Positioner, J. Clin. Orthod. (1996) 30:673-680.

Kochanek, "Interpolating Splines with Local Tension, Continuity and Bias Control," Computer Graphics, ri 18(3):33-41 (Jul. 1984). KM Oral Surgery (1945) 31 :297-30.

Kunii et al., "Articulation Simulation for an Intelligent Dental Care System," Displays 15:181-188 (1994).

Kuroda et al., Three-Dimensional Dental Cast Analyzing System Using Laser Scanning, Am. J. Orthod. Dentofac. Orthop. (1996) 110:365-369.

Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991).

Leinfelder, et al., "A New Method for Generating Ceramic Restorations: a CAD-CAM System," J. Am. 1-1 Dent. Assoc., 118(6):703-707 (Jun. 1989).

Manetti, et al., "Computer-Aided Cefalometry and New Mechanics in Orthodontics," (Article Summary in English, article in German), Fortschr Kieferorthop. 44, 370-376 (Nr. 5), 1983.

McCann, "Inside the ADA," J. Amer. Dent. Assoc., 118:286-294 (Mar. 1989).

McNamara et al., "Invisible Retainers," J. Cfin. Orthod., pp. 570-578 (Aug. 1985).

McNamara et al., Orthodontic and Orthopedic Treatment in the Mixed Dentition, Needham Press, pp. 347-353 (Jan. 1993).

Moermann et al., "Computer Machined Adhesive Porcelain Inlays: Margin Adaptation after Fatigue Stress," IADR Abstract 339, J. Dent. Res., 66(a):763 (1987).

Moles, "Correcting Mild Malalignments—As Easy As One, Two, Three," AOA/Pro Corner, vol. 11, No. 1, 2 pages (2002).

Mormann et al., "Marginale Adaptation von adhasuven Porzellaninlays in vitro," Separatdruck aus: Schweiz. Mschr. Zahnmed. 95: 1118-1129, 1985.

Nahoum, "The Vacuum Formed Dental Contour Appliance," N. Y. State Dent. J., 30(9):385-390 (Nov. 1964).

Nash, "CEREC CAD/CAM Inlays: Aesthetics and Durability in a Single Appointment," Dent. Today, 9(8):20, 22-23 (Oct. 1990).

Nishiyama et al., "A New Construction of Tooth Repositioner by LTV Vinyl Silicone Rubber," J. Nihon Univ. Sch. Dent., 19(2):93-102 (1977).

Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.

Pinkham, "Foolish Concept Propels Technology," Dentist, 3 pages total, Jan./Feb. 1989.

Pinkham, "Inventors CAD/CAM May Transform Dentistry," Dentist, 3 pages total, Sep. 1990.

Ponitz, "Invisible Retainers," Am. J. Orthod., 59(3):266-272 (Mar. 1971).

Procera Research Projects, "Procera Research Projects 1993—Abstract Collection," pp. 3- 7; 28 (1993).

Proffit et al., Contemporary Orthodontics, (Second Ed.), Chapter 15, Mosby Inc., pp. 470-533 (Oct. 1993).

Raintree Essix & Ars Materials, Inc., Raintree Essix, Technical Magazine Table of contents and Essix Appliances,<http://www.essix.com/magazine/defaulthtml> Aug. 13, 1997.

Redmond et al., "Clinical Implications of Digital Orthodontics," Am. J. Orthod. Dentofacial Orthop., 117(2):240-242 (2000).

Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).

Rekow, "CAD/CAM in Dentistry: A Historical Perspective and View of the Future," J. Can. Dent. Assoc., 58(4):283, 287-288 (Apr. 1992).

Rekow, "Computer-Aided Design and Manufacturing in Dentistry: A Review of the State of the Art," J. Prosthet. Dent., 58(4):512-516 (Oct. 1987).

Rekow, "Dental CAD-CAM Systems: What is the State of the Art?", J. Amer. Dent. Assoc., 122:43-48 1991.

Rekow et al., "CAD/CAM for Dental Restorations—Some of the Curious Challenges," IEEE Trans. Biomed. Eng., 38(4):314-318 (Apr. 1991).

Rekow et al., "Comparison of Three Data Acquisition Techniques for 3-D Tooth Surface Mapping," Annual International Conference of the IEEE Engineering in Medicine and Biology Society, 13(1):344-345 1991.

Rekow, "Feasibility of an Automated System for Production of Dental Restorations, Ph.D. Thesis," Univ. of Minnesota, 244 pages total, Nov. 1988.

Richmond et al., "The Development of a 3D Cast Analysis System," Br. J. Orthod., 13(1):53-54 (Jan. 1986).

Richmond et al., "The Development of the PAR Index (Peer Assessment Rating): Reliability and Validity," Eur. J. Orthod., 14:125-139 (1992).

Richmond, "Recording The Dental Cast in Three Dimensions," Am. J. Orthod. Dentofacial Orthop., 92(3):199-206 (Sep. 1987).

Rudge, "Dental Arch Analysis: Arch Form, A Review of the Literature," Eur. J. Orthod., 3(4):279-284 1981.

(56) References Cited

OTHER PUBLICATIONS

Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances-Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances-Pro Lab product information for patients,<http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).

Van Der Zel, "Ceramic-Fused-to-Metal Restorations with a New CAD/CAM System," Quintessence Int., 24(11):769-778 (1993.
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987.
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. Of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
You May Be a Candidate for This Invisible No-Braces Treatment, Allesee Orthodontic Appliances-Pro Lab product information for patients, 2 pages (2002).

* cited by examiner

METHOD FOR MANIPULATING A DENTAL VIRTUAL MODEL, METHOD FOR CREATING PHYSICAL ENTITIES BASED ON A DENTAL VIRTUAL MODEL THUS MANIPULATED, AND DENTAL MODELS THUS CREATED

CROSS-REFERENCE

This application is a Continuation of U.S. application Ser. No. 15/388,580, filed Dec. 22, 2016, now U.S. Pat. No. 10,143,541, issued Dec. 4, 2018, which is a Continuation of U.S. application Ser. No. 14/882,312, filed Oct. 13, 2015, now U.S. Pat. No. 9,549,794, issued Jan. 24, 2017, which is a Continuation of U.S. application Ser. No. 14/324,784, filed Jul. 7, 2014, now U.S. Pat. No. 9,186,228, issued Nov. 17, 2015, which is a Continuation of U.S. application Ser. No. 13/716,008, filed Dec. 14, 2012, now U.S. Pat. No. 8,805,563, issued Aug. 12, 2014, which is a Continuation of U.S. application Ser. No. 13/227,435, filed Sep. 7, 2011, now U.S. Pat. No. 8,359,115, issued Jan. 22, 2013, which is a Continuation of U.S. application Ser. No. 12/654,762, filed Dec. 31, 2009, now U.S. Pat. No. 8,041,439, issued Oct. 18, 2011, which is a Continuation of U.S. application Ser. No. 12/222,287, filed Aug. 6, 2008, now U.S. Pat. No. 7,734,368, issued Jun. 8, 2010, which is a Continuation of U.S. application Ser. No. 11/349,124, filed Feb. 8, 2006, now U.S. Pat. No. 7,555,403, issued Jun. 30, 2009, which claims the benefit of prior U.S. Provisional Patent Application No. 60/699,499, filed Jul. 15, 2005, the contents of each of which are hereby incorporated by reference in their entirety.

FIELD OF THE INVENTION

This invention relates to dentistry and in particular to computer-aided methods associated with prosthodontics.

BACKGROUND OF THE INVENTION

There are many procedures associated with the oral cavity in which a precise three-dimensional representation of the cavity is very useful to the dental practitioner.

Such representations enable the practitioner to study the cavity of individual patients in a similar manner to the study of the traditional plaster model. More importantly, three-dimensional numerical entities of the dental cavity also allow the practitioner to study methods or approaches when dealing with particular dental problems of any given patient, and for the design of physical entities in relation therewith. For example, in prosthodontics, a computer model of a patient's teeth may be manipulated to provide machining data to manufacture a physical model of the intra oral cavity, and/or to design and manufacture a coping and/or a prosthesis.

A parameter used in the design and manufacture of a dental prosthesis, such as a crown or bridge, is the finish line, or transition boundary between the prosthesis and the dental preparation, and this needs to be precisely defined in three-dimensions. Obtaining the finish line coordinates from a computer virtual model is more efficient and often more accurate than from a plaster cast, and moreover facilitates the production of such a prosthesis, for example via CNC machining, rapid prototyping, or other computerized technologies, if desired.

However, it is often the case that when scanning the intra oral cavity to obtain 3D data of the preparation and finish line on which the virtual model is based, part of the finish line, and possibly also the shoulder and other parts of the preparation, may be obscured by soft tissues such as the gum that, no longer being pushed by the dental surfaces that have been removed, deform to cover at least a part of the finish line on the prepared dental site.

Additionally or alternatively, part or all of the finish line may be obscured by other agents, including, for example, accumulation of one or more of saliva, blood, lubricant used with a dental drill, debris resulting from working the, dental site, and so on.

SUMMARY OF THE INVENTION

Herein, "dental material" refers to any material associated with dental structures of the intra oral cavity, including but limited to natural dental materials such as for example enamel, dentine, pulp, dental roots, and non-natural dental materials such as for example metallic and non-metallic fillings, restorations, crowns, bridges, copings, preparations, and so on.

Herein, "dental clinic" refers to the interface between a dental practitioner and a patent, and thus includes any physical entity, in particular a clinic, in which there is interaction between a dental patient and a dental practitioner. While "dental practitioner" typically refers to a dentist, doctor or dental technician, it also includes herein all other caregivers, including for example dental surgeons, orthodontists, prosthodontists, or any other caregiver that may interact with a dental patient during the course of a dental treatment, or that may be involved in determining, preparing or providing dental treatment to a patient, particularly prosthodontic treatment. While "dental patient" or "patient" typically refers to a person requiring the dental services of a dental practitioner, it also includes herein any person regarding whom it is desired to create a 3D numerical model of the intra oral cavity thereof, for example for the purpose of practicing the same or for carrying out research.

The term "prosthesis" is herein taken to include any restoration and any onlays, such as crowns and bridges, for example, and inlays, such as caps, for example, or veneering, or any other artificial partial or complete denture.

The term "virtual", applied herein with respect to models, manipulation of models, and so on, for example, refers to being created, simulated, or carried out by means of a computer or computer network or the like.

While the term "preparation" typically refers to the stump and including the finish line and shoulder that is left of the tooth that is to be replaced by the prosthesis typically a crown—and on which the crown is to be mounted, the term herein also includes artificial stumps, pivots, cores and posts, or other devices that may be implanted in the intraoral cavity in such a position or in a position that is optimal for implanting the crown.

The term "prosthodontic procedure" refers, inter alia, to any procedure involving the intraoral cavity and directed to the design, manufacture or installation of a dental prosthesis at a dental site within the intraoral cavity, or a real or virtual model thereof, or directed to the design and preparation of the dental site to receive such a prosthesis.

The term "numerical entity" is used herein synonymously with virtual model, 3D model, and other such terms, and relates to a virtual representation in a computer environment of a real object, such as for example a dentition or at least a part of intraoral cavity, or of a real model thereof.

The term "physical entity" is used herein to refer to a physical dental object included but not limited to a physical dental model of part or all of the dentition of the intraoral cavity including dies, a coping, a prosthesis, and so on.

The term "scanning" and its analogues refer to any procedure directed at obtaining 3D topographic data of a surface, particularly of a dental surface, and thus includes mechanical methods, typically based on 3D probes for example, optical methods, including for example confocal methods, for example as disclosed in WO 00/08415, the contents of which are incorporated herein in their entirety by reference, or indeed any other method.

The terms "tool" and "machining tool" are taken herein to include any tool that is adapted for material removal, and may include inter alia mechanical tools such as drills for example, laser tools such as for example laser drills or cutters, ultrasonic tools such as for example ultrasonic cutters, and so on. Preferably, the machining paths and material removal characteristics of such tools can be finely controlled, typically by computer means.

The present invention relates to a method for manipulating a virtual dental model, comprising:—
- (a) providing a 3D virtual model of at least a portion of an intraoral cavity comprising a preparation having a finish line, wherein at least a portion of the finish line is obscured;
- (b) manipulating said 3D virtual model in the vicinity of said obscured portion of said finish line in a virtual manner such as to create an auxiliary 3D virtual model corresponding to said obscured portion of said finish line;
- (c) providing topographical data of the finish line from the virtual model and the said auxiliary virtual model.

The virtual model may be provided by scanning the intra-oral cavity in vivo, or by any other suitable method.

The finish line may be partially or fully obscured by any obscuring entity or matter, including, but not limited to, deformed soft tissues, accumulation of one or more of saliva, blood, lubricant used with a dental drill, debris resulting from working the dental site, and so on.

The method can further comprise:
- (d) identifying in said 3D virtual model a first virtual model part representing a dental site comprising said preparation and a second virtual model part representing at least soft tissues in abutting virtual contact with said first virtual model part;
- (e) manipulating said 3D virtual model such as to separate said first virtual model part from said second virtual model part;
- (f) manipulating said first virtual model part such as to create said auxiliary virtual model.

Step (d) may be carried out substantially in an automated manner when said 3D virtual model provided at step (a) comprises color data associated with 3D topographic data, wherein said identification of said first virtual model part and said second virtual model part is based on color differences therebetween.

The second virtual model part may comprise said obscured portion of said finish line.

The step of manipulating said first virtual model part such as to create said auxiliary virtual model corresponding to said obscured part of said finish line may comprise:
- (g) providing at least one cross section of said 3D virtual model along a working plane inclined to the occlusion plane, at least within said obscured finish line portion, said cross-section comprising a first cross-section profile representing said preparation and a second cross-section profile representing obscuring matter in abutting virtual contact with said first cross-section profile at a contact region;
- (h) extrapolating said first cross-section profile from said contact region to provide a third cross-section profile representing at least an approximation of a corresponding cross-section of said dental site below said obscuring matter and identifying therein a corresponding element of said obscured finish line portion.

By "extrapolating" is meant any suitable method, which may be numerical, graphical, intuitive, and so on, based on the first cross-section profile.

Optionally, additional data relating to the emerging profile, gum line and so on may also be provided.

In step (g), said at least one cross section of said virtual model may be provided along a corresponding plane inclined generally orthogonally to the occlusion plane.

Alternatively, the working planes may be parallel or non parallel one to another, and/or at any desired angle to the occlusal plane.

Alternatively, any other method, for example any suitable graphical method, may be used for defining the geometry of at least the obscured finish line portion.

The method optionally further comprises creating a trimmed first model part comprising said first model part and said auxiliary virtual model, and also manipulating said second model part to remove surface data thereof corresponding to said auxiliary virtual model and creating a trimmed second model part.

The said trimmed first model part can be further manipulated such as to include a virtual model base projecting therefrom, and said trimmed second model part can also be manipulated such as to include a model well substantially complementary to said model base. The virtual model base may optionally comprises a depth dimension extending substantially orthogonally to an occlusial plane of the intra oral cavity, and said virtual model base may of substantially uniform cross-sectional profile along a depth thereof. Alternatively, the base may be convex-shaped, conical, fustoconical, or any other suitable shape.

The perimeter of the virtual base, when viewed along said depth direction may correspond to any one of a finish line or demarcation line of the trimmed first model. Alternatively, the perimeter of the virtual base, when viewed along said plan direction, may correspond to any one of circle, oval, polygon or any suitable shape.

Optionally, one of said virtual model base and said virtual model well further comprises at least one virtual projection, and the other one of said virtual model base and said virtual model well further comprises a virtual socket structure for virtually receiving said at least one projection. In other words, the virtual socket is substantially complementary in form and size to the corresponding projection. The projection can also take the form of a laterally projecting tab that is receivable in a socket structure that is formed as a longitudinal channel on the side of the well.

The said at least one virtual projection and virtual socket structure are arranged with respect to said virtual base and virtual well such that said virtual base can be virtually received in said virtual well, in only one orientation with respect thereto.

The method optionally further comprises the step of preparing computer instructions for controlling operation of a computer controlled manufacturing machine for creating physical models corresponding to said trimmed first and second virtual model parts respectively including said virtual model base and said virtual model well. The said computer instructions may be directed to carrying out a material removal operation on at least one material blank to create said physical models, for example. This material removal operation may comprise CNC (Computer Numerical Control) machining including milling of said at least one material blank.

The present invention also relates to a method for manufacturing a dental model, comprising:—
(a) providing a trimmed first virtual model part and a trimmed second virtual model part, according to the invention, corresponding to at least one dental site;
(b) preparing computer instructions for controlling operation of a computer controlled manufacturing machine for creating physical models corresponding to said trimmed first and second virtual model parts respectively including said virtual model base and said virtual model well; and
(c) executing said computer instructions on said computer controlled manufacturing machine and creating a set of physical models comprising a trimmed first physical model part and a trimmed second physical model part corresponding to said trimmed first and second virtual model parts respectively including said virtual model base and said virtual model well.

A dental site relates to a location in the intra oral cavity comprising one or more teeth of interest. One or more such teeth may include a preparation.

The computer instructions may be directed to carrying out a material removal operation on at least one material blank to create said physical models. The material removal operation may comprise CNC machining of said at least one material blank.

The method for manufacturing a dental model may be applied to a single dental site, or alternatively to a plurality of dental sites on at least one jaw of an intra oral cavity. Inn the latter case particularly, the trimmed second virtual model corresponding to each said dental site can be suitably joined in a virtual manner to provide a global virtual model of said jaw. In such a manner it is possible to manufacture a model of one or both partial of full jaws, in which any number of the teeth therein, whether or not they have a preparation, are formed as separate models which can be removed and replaced in the jaw model. Tooth models in cases where then tooth is complete or in which there is no obstruction can be manufactured in a similar manner as described above, mutatis mutandis, with the main differences that no recreation or reconstruction of obscured portions thereof need to be performed.

The invention also relates to a method for at least one of designing and manufacturing a dental coping, using a trimmed first virtual model according to the invention.

The invention also relates to a method for at least one of designing and manufacturing a dental prosthesis, using a trimmed first virtual model according to the invention.

The invention also relates to a physical model set of at least a portion of an intra oral cavity, comprising a trimmed first physical model part and a trimmed second physical model part corresponding to a trimmed first virtual model part and a trimmed second virtual model part according to the invention.

The present invention also relates to systems for manipulating virtual dental models and for manufacturing physical dental entities based on a virtual dental model manipulated according to the invention. Such systems may include a microprocessing unit comprising suitable software for carrying out the method of the invention, an interface, such as for example a mouse, tablet, keyboard and so on, a display, and a data input module for inputting 3D data of the intra oral cavity.

Thus, according to the invention, a 3D virtual model of an intra oral cavity in which at least a part of a finish line of a preparation is obscured is manipulated in virtual space by means of a computer or the like to create, recreate or reconstruct finish line data and other geometrical corresponding to the obscured part. Trimmed virtual models, and trimmed physical models, can then be created utilizing data thus created. The virtual models and/or the physical models may be used in the design and manufacture of copings or of prostheses.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF EXEMPLARY EMBODIMENTS

Figure 1:
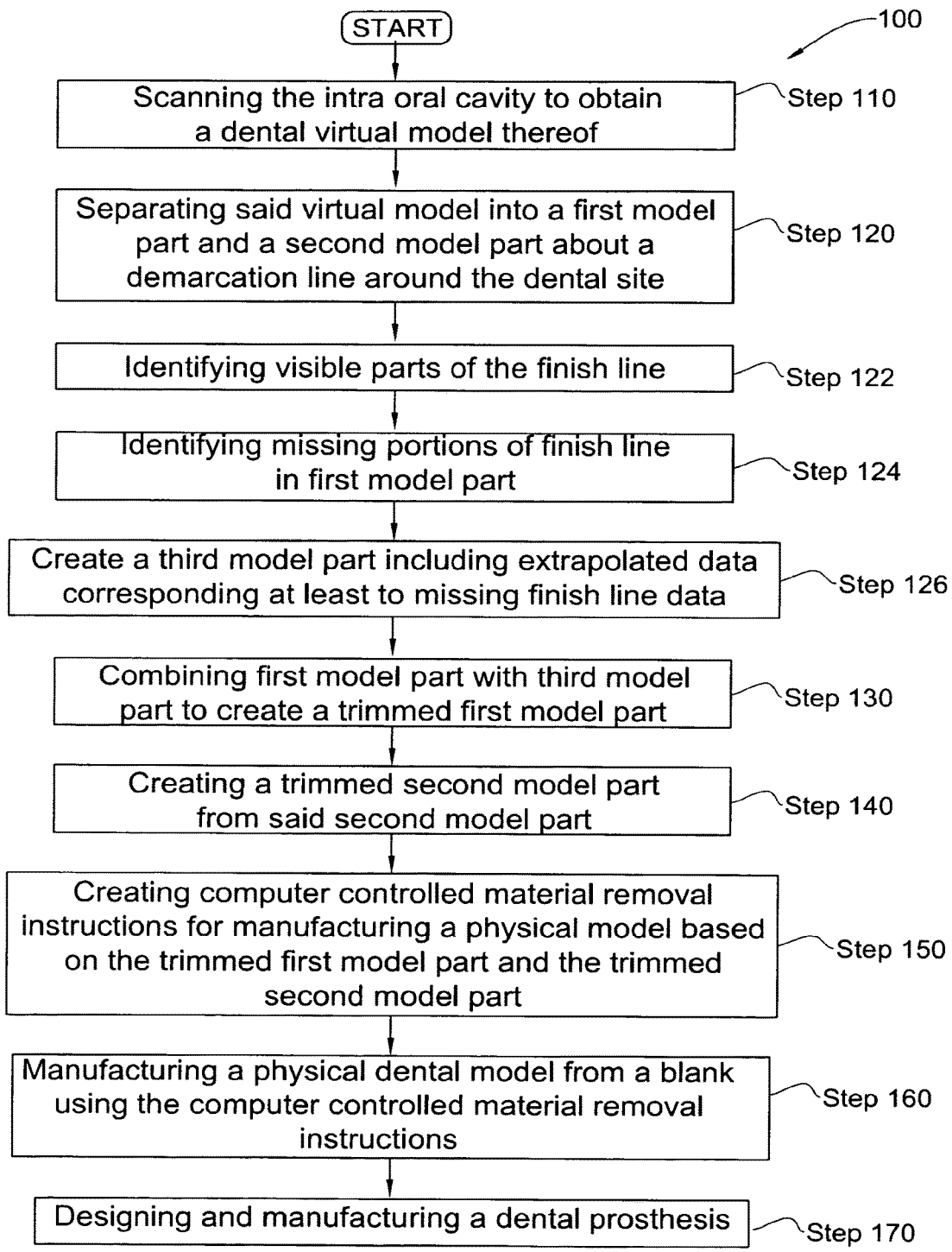
FIG. 1 shows, by way of a flow chart, a method for manipulating a dental virtual model in accordance with an embodiment of the invention.

A computer-based method for manipulating a virtual dental model, particularly useful for defining a finish line (also referred to herein as "margin line"), according to the invention is illustrated in FIG. 1. Accordingly, acquiring an accurate 3D representation (herein also referred to as "three-dimensional model", "3D model", "virtual model" and the like) of the intraoral cavity is the first step 110 that is carried out by the method 100. This first virtual model is generally designated with the numeral 500 in the accompanying figures.

The target parts of the intraoral cavity that are to be scanned are first identified. The target parts are the parts (also referred to interchangeably as zones or areas) of the intraoral cavity 200 which form the focus of a particular dental procedure for a particular patient and regarding which it is desired to obtain the 3D topographical or surface data thereof. The target parts typically include the part of the tooth or the teeth on which a particular prosthodontic procedure is to be performed, and in some cases may include partial or the full mandibular or maxillary arches, or both arches. For example, the procedure may be a prosthodontic procedure involving a crown or bridge prosthesis to be designed and fabricated for fitting onto a preparation at a particular dental site.

Figure 3:
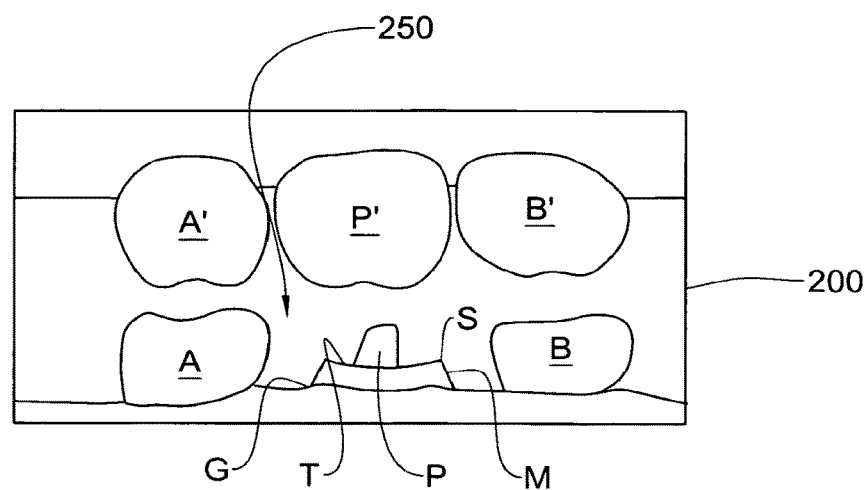
FIG. 3 schematically illustrates a portion of the intra oral cavity requiring a prosthesis.

The method of the invention may be applied after the dental site 250 has been prepared, at least partially for a prosthesis. For a crown prosthesis, the dental site 250 includes a single tooth that is prepared for receiving the prosthesis, while for a bridge prosthesis, there are typically two dental sites, each of which includes a tooth that needs to be prepared, in order to anchor the prosthesis. Referring to FIG. 3, the preparation of each tooth requires the dental practitioner to perform a dental material removal operation at the dental site 250, creating a preparation P having a central anchoring stump joined via shoulder T to a finish line S that circumscribes the stump and separates the preparation from the emerging profile M, which in turn extends to the gum line G.

When the target area including the dental site 250 is scanned very accurately, it is possible for the internal surface of a corresponding coping to be correspondingly accurately designed. Ancillary parts of the intraoral cavity are also typically included in the scan, and comprise parts of the adjacent and opposed teeth, principally teeth A, B, P', and often to a lesser extent teeth A' and B' (which are adjacent to the opposite tooth P') or parts thereof. Typically, but not necessarily, the resolution of the scanned data for the ancillary parts may be less than for the dental site itself, since the manufacturing accuracy required for the external surfaces of the crown prosthesis (the design of which is dependent on the dental surfaces of the ancillary parts) may be substantially less than for the internal surface of the coping (or of the crown if this is monolithic).

Figure 4:
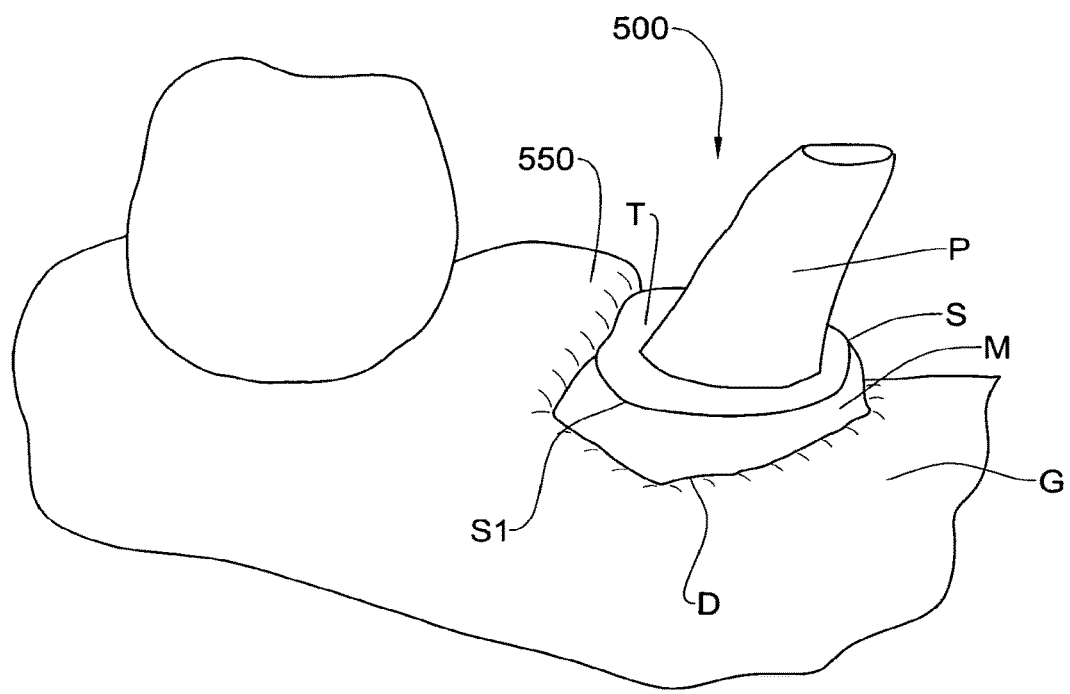
FIG. 4 illustrates a virtual model of the intra oral cavity as viewed with 3D attributes.

The present invention is particularly applicable to situations in which at least a part of the finish line S and possibly a part of the shoulder T is obscured by other material 550, typically either soft tissue (typically gums) and/or a retraction wire (FIG. 4) and/or other foreign matter. Thus, the virtual model 500 obtained by the scanning process lacks finish line data (and also emerging profile data) at the obscured portions of the finish line.

Figure 2:
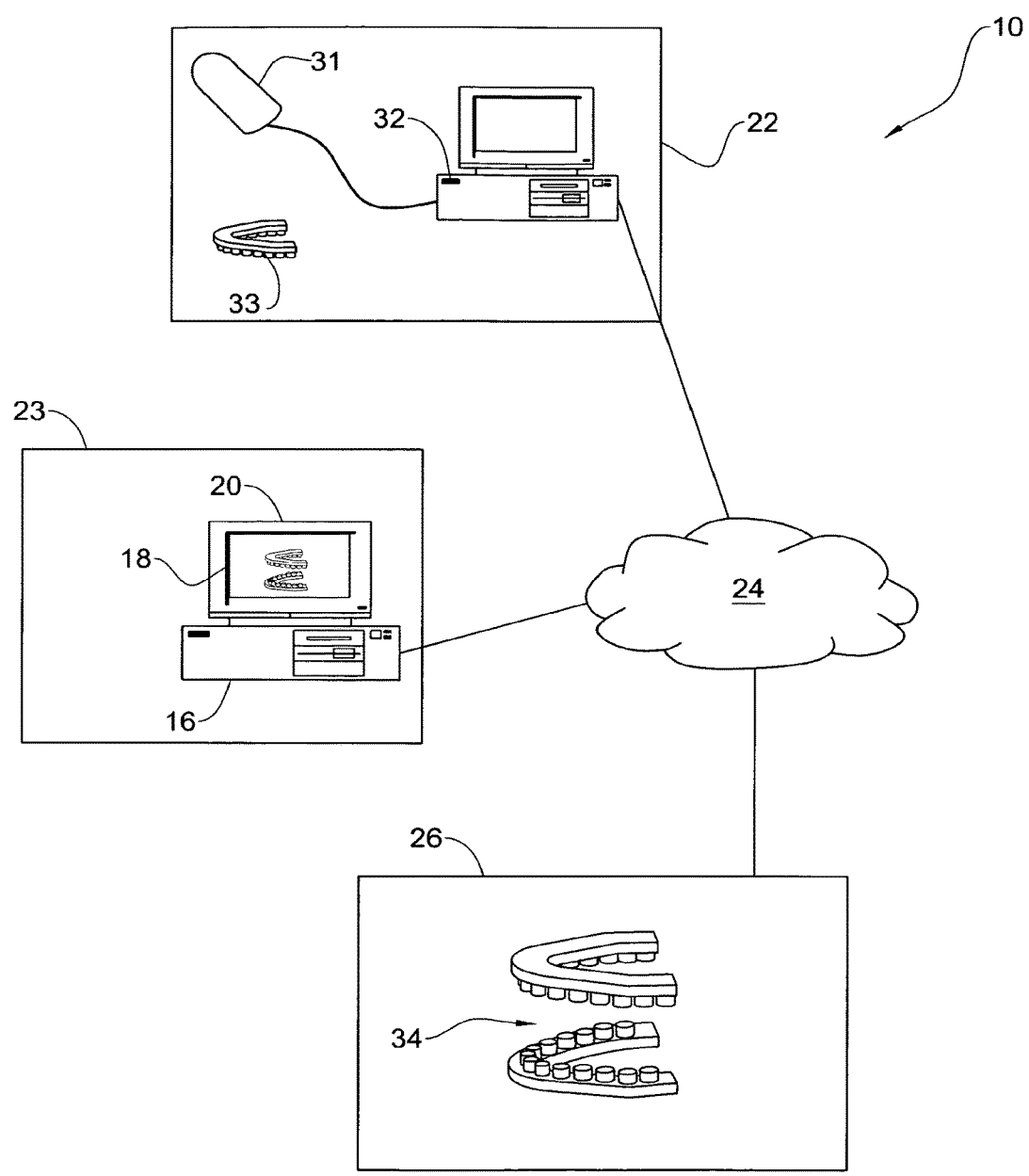
FIG. 2 shows various elements of a system used for providing and manipulating a virtual dental model according to the invention.

The 3D digitized data of the intraoral cavity, including the dentition and associated anatomical structures of a patient, may be provided using any suitable equipment for scanning a patient's teeth. Referring to FIG. 2, this is usually done at a dental clinic 22 by the dentist or other dental practitioner. The dental clinic 22 is typically linked to one or more dental labs 26, and possibly also to a dental service center 23 via a communication means or network such as for example the Internet or other suitable communications medium such as an intranet, local access network, public switched telephone network, cable network, satellite communication system, and the like, indicated by the cloud at 24. The dental lab 26 is particularly adapted for defining the finish line, as well as for other tasks such as designing prostheses, designing and manufacturing physical models of the dentition, and possibly also for manufacturing at least an external profile of the prostheses. The dental service center 23 is particularly adapted for manufacturing dental hardware that requires a very high degree of precision, for example inner surfaces of prostheses that are required to match external surfaces of copings, and possibly also the copings themselves.

Such scanning equipment may include any suitable optical scanner, for example, a hand-held scanner 31 that is used by the practitioner to acquire the 3D data. Advantageously, a probe for determining three dimensional structure by confocal focusing of an array of light beams may be used, for example as manufactured under the name of CB-CAD or as disclosed in WO 00/08415, the contents of which are incorporated herein by reference in their entirety. The 3D data obtained by the probe may then be stored in a suitable storage medium, for example a memory in a computer workstation 32. Typically, the 3D data is sent over a suitable communication network 24 to the dental lab 26, for further processing, as described below. Optionally, the to the dental service center 23 the 3D data may be sent via communication network 24 to the dental lab 26, for the further processing.

Optionally, and preferably, color data of the intraoral cavity is also provided together with the 3D data, and thus the virtual model comprises coordinates and color information of the dental surfaces scanned. Examples of such scanners are disclosed in co-pending application entitled "METHOD AND APPARATUS FOR COLOUR IMAGING A THREE-DIMENSIONAL STRUCTURE", filed on 17 Jun. 2005 and published under US 2006-0001739, and which is assigned to the present Assignee. The contents of the aforesaid co-pending application are incorporated herein by reference in their entirety.

Alternatively, the clinic 22 may include equipment for obtaining a negative casting of a patient's teeth. In this case, the negative cast or impression is taken of the patient's teeth, in a manner known in the art, and this negative model 33 is dispatched to one of the dental labs 26 that is equipped to prepare from the negative model a positive cast 34 suitable for scanning. The positive cast 34 may be scanned at the dental lab 26 by any method known in the art, including using the aforesaid probe manufactured under the name of CB-CAD or as disclosed in WO 00/08415. The 3D data is then transmitted over the network 24 to the service center 23. Alternatively, the positive cast 34 may be dispatched to the service center 23 by the dental clinic 22 and scanned at the service center to obtain the 3D data. Alternatively, the service center 23 produces a positive model 34 from the negative model 33 and is scanned thereat, or sent to the dental clinic 22 to be scanned thereat. Alternatively, the negative model 33 is scanned, either at the dental lab 26 or at the service center 23.

Alternatively, the negative model 33 provided by the clinic 22 is sent to the service center 23, either directly by the clinic 22, or indirectly via the dental lab 26, and a composite positive-negative model may be manufactured from the original negative model. Thereafter, the positive-negative model may be processed to obtain 3D digitized data, for example as disclosed in U.S. Pat. No. 6,099,314, assigned to the present Assignee, and the contents of which are incorporated herein in their entirety.

Alternatively, the 3D digitized data may be obtained in any other suitable manner, including other suitable intra oral scanning techniques, based on optical methods, direct contact or any other means, applied directly to the patient's dentition. Alternatively, X-ray based, CT based, MM based, or any other type of scanning of the patient or of a positive and/or negative model of the intra-oral cavity may be used. The dimensional data may be associated with a complete dentition, or of a partial dentition, for example such as a preparation only of the intra oral cavity.

Once the 3D digitized data is obtained, the next steps 120-126, which are performed with the aid of a suitable computer, enable the full finish line S to be defined, which enables the subsequent design and manufacture of an appropriate dental prosthesis, step 170, to be followed by the installation of the appliance in the oral cavity of the patient, step 180. These steps are generally carried out in the dental lab 26, though may be executed at the dental clinic 22 or service center 23 with the appropriate equipment and expertise.

Figure 5:
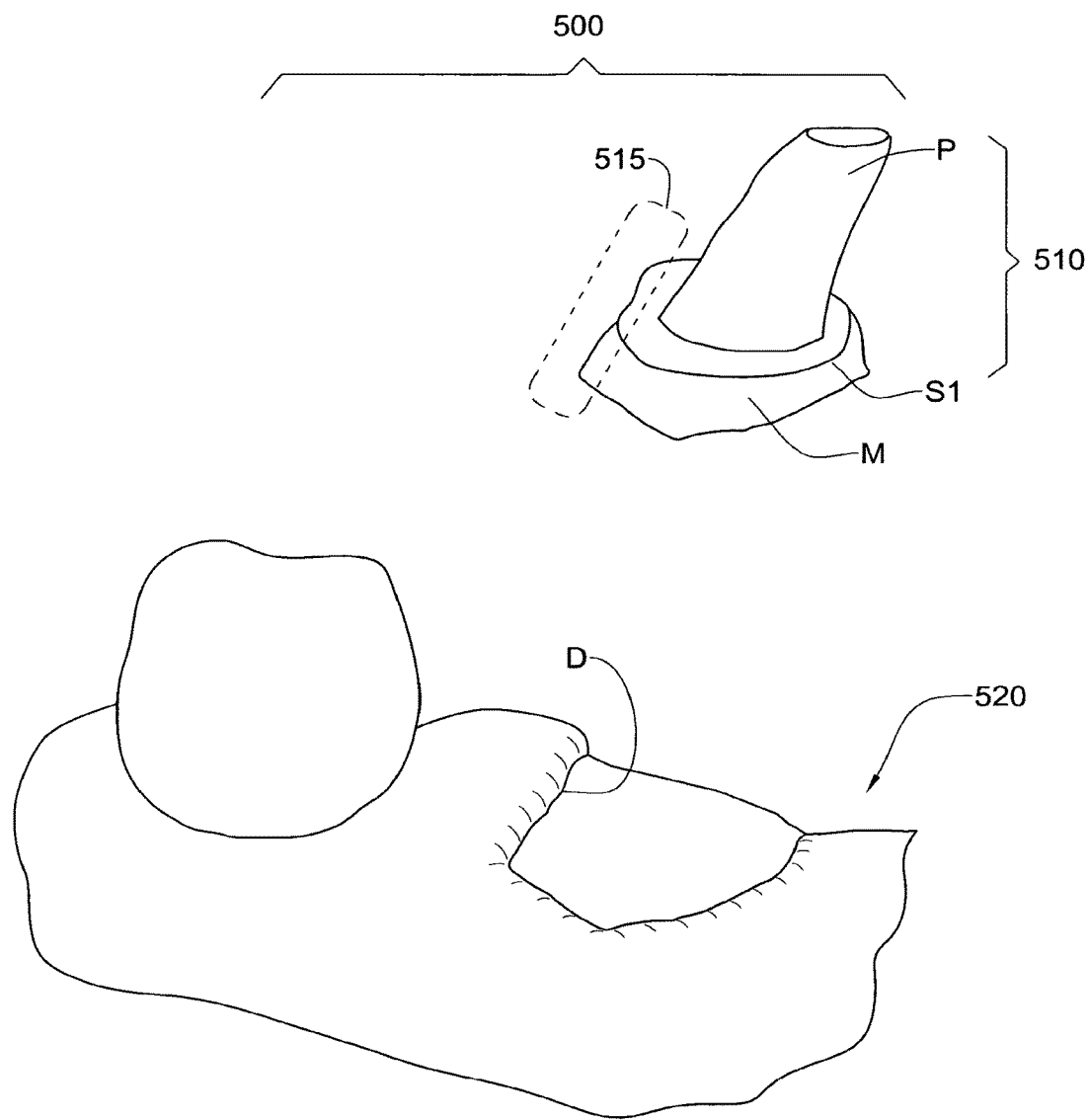
FIG. 5 illustrates the virtual model of FIG. 4 separated into a first model part and a second model part.

Referring to FIG. 1 and FIG. 5, in step 120 the virtual model 500 is manipulated by means of a suitable computer in order to separate a first part 510 of the virtual model representing the dental site 250, in particular the hard tissues thereof, from a second part 520 of the virtual model, typically the remainder of the model 500, and including at least the data representing the soft tissues and possibly foreign matter such as retraction wires, etc, that surround the first part 510. Thus, this step isolates the surface data corresponding to the parts of the emerging profile M, the portion S1 of finish line S and preparation P that are not obscured by soft tissue or foreign objects including, for example, saliva, blood, lubrication fluid, debris and so on. This step may be performed manually with a computer, typically interactively, by a user, by means of suitable graphics software, for example, that display model 500, and an interface such as a mouse, keyboard, and so on, for example. The user may visually identify a demarcation profile D (FIGS. 4 and 5) that separates model parts 510 and 520, and for this purpose the model 500 as displayed may be manipulated and viewed at any attitude, rotational angle, magnification etc. as desired. Suitable software for manipulating a virtual model in this manner are well known in the art and will not be described further herein. Then, the user virtually marks a number of points on the displayed model 500 which are converted by the computer into corresponding 3-dimensional coordinates of the demarcation profile, and suitable interpolation between points completes the definition of the demarcation profile D. Then, the computer can divide the model 500 along profile D into model parts 510 and 520.

Alternatively, and particularly when the virtual model 500 also comprises color data corresponding to the topographical data, the color differences between the relatively white hard dental surfaces of the dental site 250 and the relatively pink/red gum tissue and/or the retractor wire or other foreign matter, may be used to separate the model 500 into model parts 510 and 520 in an automated manner. Examples of such methods are disclosed in co-pending application entitled "METHOD FOR PROVIDING DATA ASSOCIATED WITH THE INTRAORAL CAVITY", filed on 17 Jun. 2005 and published under US 2005/0283065, and which is assigned to the present Assignee. The contents of the aforesaid co-pending application are incorporated herein by reference in their entirety.

Figure 6:
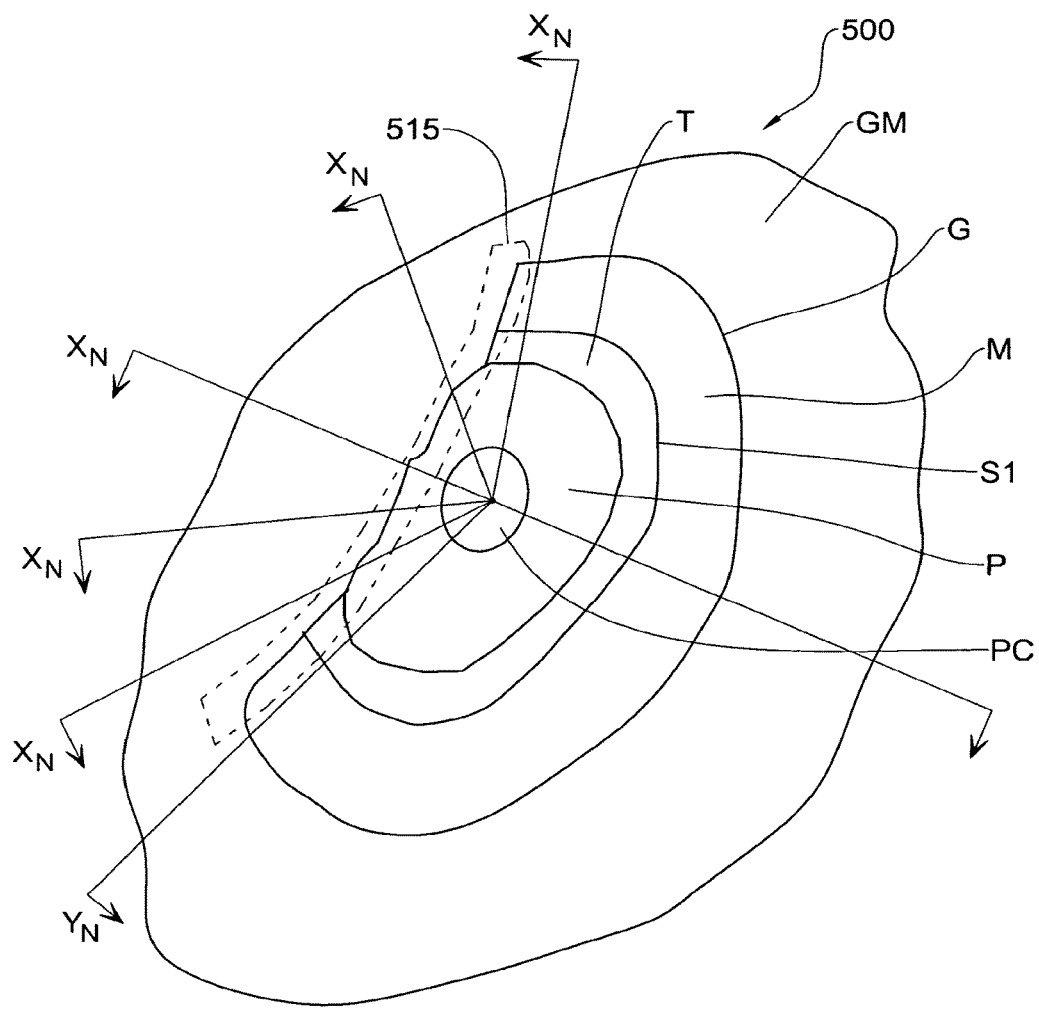
FIG. 6 illustrates in plain view the first model part of FIG. 5 including a plurality of planes normal to this view.

In the next step 122, and referring also to FIGS. 5 and 6, the exposed portions S1 of the finish line S, i.e., the portions that are visible, are identified and marked in the first model part 510. By "marking" is included that an attribute is added to the data points corresponding to these portions of the model 510, so that these portions may be highlighted and/or further manipulated, displayed etc. as a unit. This identification and marking may be done manually, by means of a display and interface, similarly to that described for step 120 above, mutatis mutandis. Alternatively, for example, this may be accomplished in an automated manner, or at least semi-automated manner, by suitably manipulating the first model part 510 by means of a suitable algorithm or the like. For example, the computer in which the method is being executed may be programmed to identify within the data of the first model part 510, relatively sharp changes in geometry, as is the case in the change of cross-sectional profile between the emerging profile M, the finish line S and shoulder T. Alternatively, other rules may be incorporated to provide the exposed portions S1 of the finish line S.

In the next step 124, the areas of the first model part 510 that do not include a finish line are identified and optionally marked. This identification and marking may be done manually, by means of a display and interface, similarly to that described for step 122 above, mutatis mutandis. Alternatively, the computer may attempt to determine in what manner the exposed portions S1 does not complete a closed geometrical form, and thus determines which parts of the geometric form are "missing". The computer can then compute in an automated manner which part of the 3-dimensional space generally occupied by the first model part 510 would include these "missing" parts.

In any case, once the missing portions, herein generally designated as 515, are identified and optionally marked in a suitable with reference to the first model part 510, the next step 126 is to create 3-dimensional representations of the missing portions 515, i.e., a third model part. This can be accomplished in a number of different ways. For example, and referring to FIGS. 6 and 7, the virtual model 500 is sliced about a plurality of working planes $X_N$ to provide a corresponding plurality of cross-sections CN of the model 500. These cross-sectional planes XN are typically orthogonal to the occlusal plane, and preferably pass approximately through the center portion PC of the preparation P. The plurality of planes may span an arc as viewed from above the dental site (FIG. 6) such as to include the full missing portion 515 and extend at least a little beyond the same to include at least two cross-sectional profiles that fully include emerging profile M data, finish line S data, preparation P data, gum line G data, plus gum GM data.

Figure 7:
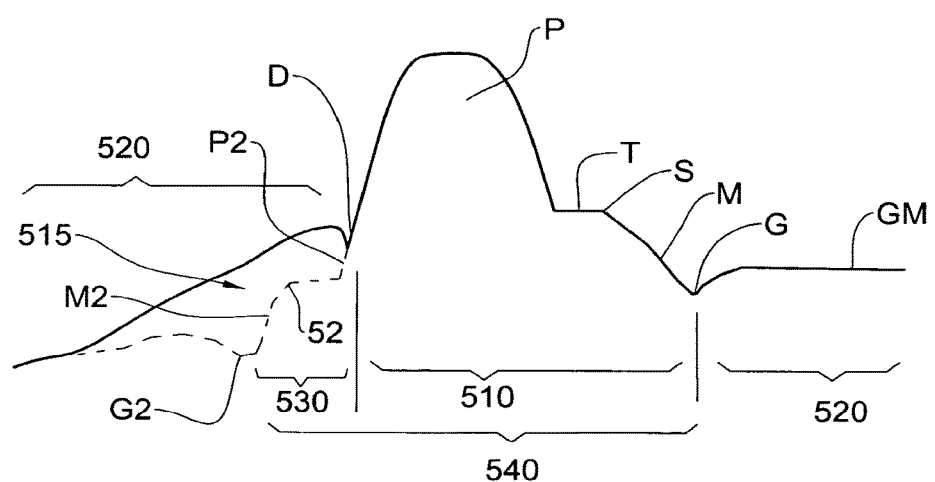
FIG. 7 illustrates a typical cross-section of the virtual first model part obtained along one of the planes in FIG. 6.

A typical cross-section $C_N$ is illustrated in FIG. 7, and shows the profile of the model 500, including first model part 510, second model part 520, and demarcation line D. Based on the user's experience and skill, the user can extrapolate where he or she considers that at least one or more of the missing finish line $S2_N$ data, missing emerging profile data M2, missing preparation data P2, and missing gum line data G2 data may be in relation to this cross-section. These missing data can then be input to the computer in which the manipulations are being carried out, for example by "clicking" with a mouse or by means of a tablet, or by any other computer aided means, at locations on the displayed cross-section where the extrapolations are to be made. Such extrapolations may be made by the user, utilizing experience and judgment as to where the missing profile may be. Alternatively, the user, knowing what type of tool was used for creating the preparation, may have a fair idea of the profile of the finish line cross section. For example, the finish line may be of any type thereof, for example knife edge, feather edge, chamfer, chamfer bevel, shoulder, shoulder bevel, and so on. Alternatively, the finish line may comprise a combination of different types around the periphery of the preparation, for example part of the finish line for a particular preparation may be knife edge, while another part may be feather edge. According to the type of finish line the user is expecting to find, the same type of profile may be applied to the missing section, and subsequently modified, manually or automatically using any suitable matching, smoothing, graphical or other type of algorithm to fit as required.

When this operation has been repeated for all the cross-sections, a 3-dimensional virtual third model part 530 corresponding to the extrapolated data may be created by the computer by properly integrating the created data, and the user may view the results together with or separately from the first model part 510.

Alternatively, the planes $X_N$ may be at any orientation and at any position with respect to the virtual model 500.

Alternatively, the missing portions may be virtually extrapolated using any suitable graphic based technique, for example, or in any other suitable manner.

In other cases, it is possible for a number of portions of the finish line to be obscured, and these portions are each treated as described above, mutatis mutandis in order to extrapolate and obtain the missing 3D data.

In some cases it is possible that the full extent of the finish line S is in fact obscured, and in such cases the method of the invention is applied for the full perimeter around the preparation P in a similar manner to that described above, mutatis mutandis, the main difference lying in that the sections $C_N$ would need to intersect the full perimeter circumscribing the preparation P.

In other case, it is possible for the finish line S to be exposed, but for a part or all of the emerging profile to the obscured. Again, the same method as above may be employed to obtain the missing 3D data, mutatis mutandis.

Alternatively, step 126 may be performed in a fully automated or semi automated manner, and suitable algorithms and/or rules such as geometrical rules may be formulated for this purpose. In any case, according to the invention, the third model part 530 may be refined over and over again until a suitable result is achieved. At each iteration, the user may inspect the third model part 530, and perhaps finely tune control parameters of the algorithm, for example, to arrive at a better solution.

In the next step 130, the third model part 530 is combined together with the first model part 510 in a virtual manner to create a completed trimmed virtual first model part 540 of the dental site, including a fully defined finish line S and preferably also a complete emerging profile M.

Figure 8:
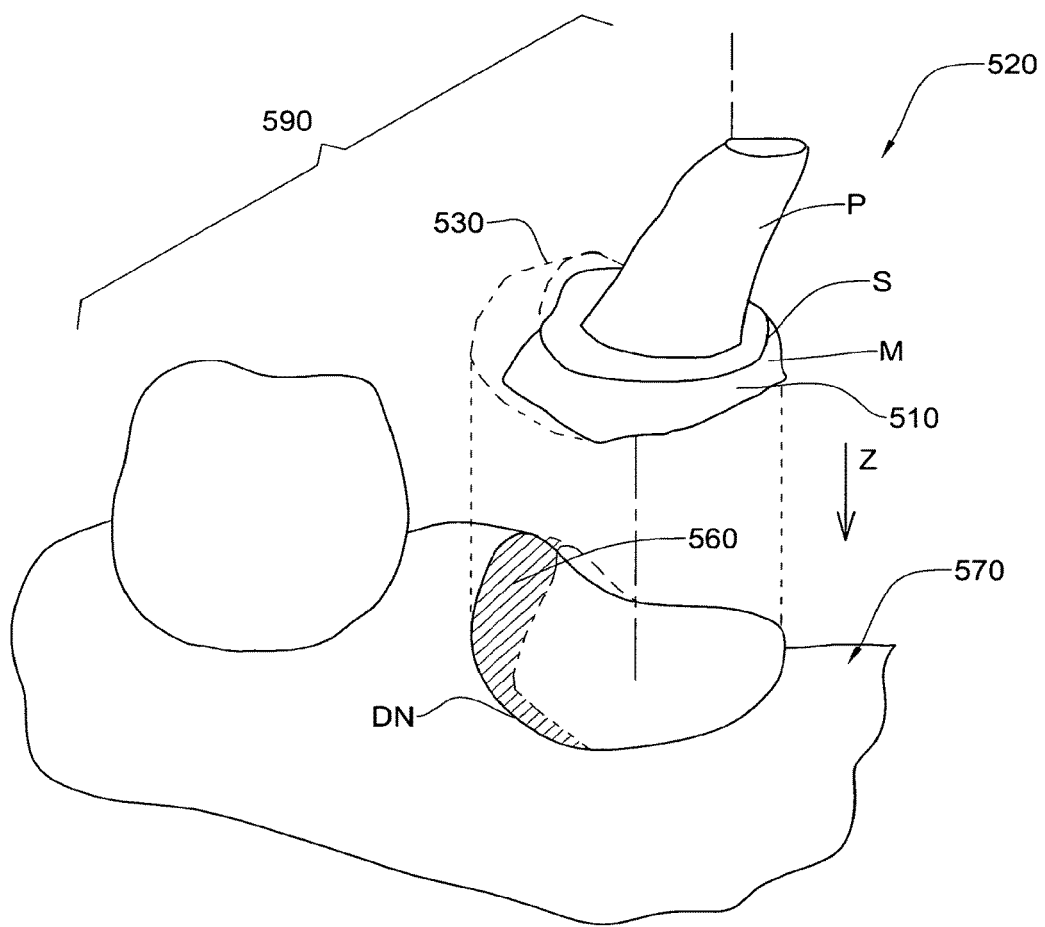
FIG. 8 illustrates the model parts of FIG. 5 after having been virtually trimmed according to the invention.

In the next step 140, and referring to FIG. 8, the second model part 520 is converted to a trimmed second model part 570 by manipulation thereof so as to effectively remove thereof excess surface data 560 that corresponds to the third model part 530, i.e., that would be superposed along a particular direction Z when joining the complete virtual model 540 to the second model part 520 such that the data corresponding to the first model part 510 in said trimmed first model part 540 "fits" in the same position as before with respect to the second model part 520. Direction Z is typically substantially orthogonal to the occlusion plane. The trimmed second model part 570 thus joins, at new demarcation line DN (at least along direction Z), the trimmed first model part 540 to form a new virtual model 590 in which the finish line S, emerging profile P, gum line G and preparation P are now fully defined.

For the case of a bridge prosthesis, the procedure may be repeated, if required, for each of the anchoring teeth.

Figure 9:
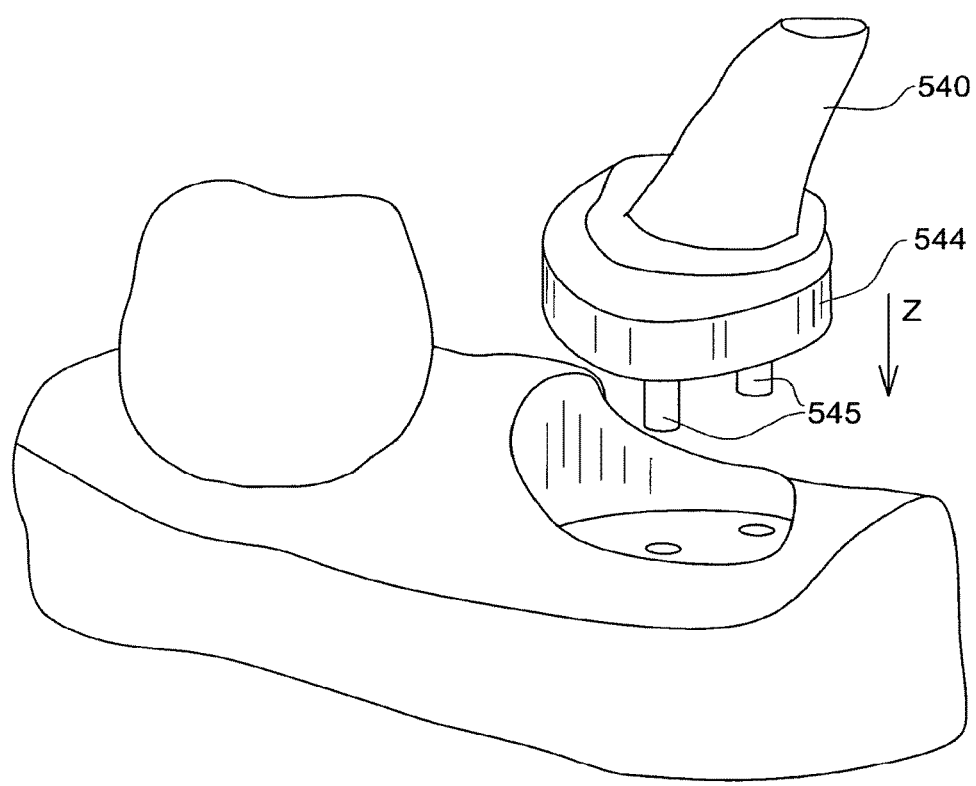
FIG. 9 illustrates a physical model of the intra oral cavity based on the trimmed virtual model of FIG. 8.

The method of the invention may be further extended to the manufacture of a physical dental model that may be used in the design and/or manufacture of a prosthesis, for example a crown or bridge prosthesis. Thus, in step 150, the trimmed first virtual model part 540 is modified to include a virtual base portion 544, typically having a cross-sectional profile identical to a plan cross-section of the complete virtual model 540 as viewed in direction Z (FIG. 9). Then, machining instructions, typically CNC milling instructions, but alternatively including any suitable computer instructions for a computer controlled material removal machine, for a material removal operation are created based on the thus modified trimmed first model part 540. The machining instructions may be further modified to include instructions for forming alignment plug members 545 extending from the bottom part of the base portion 544.

Similarly, in step 150 the trimmed second model part 570 is modified to include a well portion 574, typically having a cross-sectional profile identical to a plan view of the new demarcation line DN as viewed in direction Z, and machining instructions, typically CNC milling instructions, but alternatively including any suitable computer instructions for a computer controlled material removal machine, for a material removal operation are created based the thus modified trimmed second model part 570. Alternatively, in another aspect of the invention, rather than material removing instructions, computer instructions for creating a physical model using rapid prototyping techniques may instead be created. The machining instructions may be further modified to include instructions for forming alignment sockets 574 complementary to receiving members 545.

In general, the shape of the demarcation line, in plan or occlusal view, is asymmetric, and therefore the trimmed first model part 540 will generally fit in the trimmed second model part 570 in only one, the correct, orientation. Thus, in many cases it is possible to do without the plug members 545 and alignment sockets 574.

In any case, the base portion 544 is generally complementary to the well portion 574.

Alternatively, the trimmed first model part 540 may be based on the finish line, rather than the demarcation line, so that in plan view the outer profile of the trimmed first model part 540 corresponds to the finish line. Similarly, the profile of the well portion 574 in plan view also corresponds to the finish line, or close thereto to allow a small clearance between the trimmed first model part 540 and the trimmed second model part 570.

Alternatively, the trimmed first model part 540 may base portion 544 that is a independent of the finish line or the demarcation line, but rather circumscribes both, so that in plan view the outer profile of the trimmed first model part 540 may comprise, for example, a circle, oval, polygon, and so on. Similarly, the profile of the well portion 574 in plan view also generally corresponds to outer profile of the trimmed first model part 540. When the outer profile of the trimmed first model part 540 comprises a symmetrical shape, it may be necessary to include plug members 545 and alignment sockets 574.

Once the computer based instructions for creating the physical models are ready, the physical models corresponding to the trimmed first model part 540 and the trimmed second model part 570 may be created in a corresponding manner.

To manufacture a prosthesis such as a crown or a bridge, for example, the lab technician requires two physical jaws models mounted on an articulator or placed in the correct spatial orientation one against the other. According to the present invention, the computer controlled material removal instructions also take into consideration also the spatial relation between the two jaws and their occlusion, for example as disclosed in WO 2004/030565 assigned to the present Assignee, and the contents of this publication are incorporated herein in their entirety.

In the next step 160, a material removal operation is performed by a computer aided removal operation machine having a suitable machining tool, using any suitable CAM (Computer Aided Manufacturing) technology, typically a CNC milling machine, on a blank of material. This material is typically plaster or any other type of material commonly used for dental models, however any other suitable material may be used.

Alternatively, other techniques may be used, for example rapid prototyping, for creating the physical models. Accordingly, a physical model of the two jaws or at least a part of each of the two jaws corresponding to the virtual model 500 is manufactured, together with suitable alignment structures that ensure the proper occlusion relationship between the two components of the model representing the two jaws or the two jaw fragments.

At this point, the technician has his necessary physical model and can proceed with making the crown or the bridge.

Optionally, the physical model may be designed and manufactured comprising a plurality of individual detachable tooth models, including the target tooth, and any one or more of the surrounding and facing teeth. Similarly, when providing a physical model for use in connection with a bridge, the tooth models of one or both of the anchor teeth may be detachable from the model jaw (partial or full), and optionally, any one or more of the surrounding and facing teeth may also be detachable. When more than one tooth is detachable in the model, it is ensured that the profile of the base portion for each detachable tooth model is sufficiently different from the other base portions, and/or different plug member/alignment socket arrangements are used, to reduce the possibility of the wrong tooth model being matched with a particular well.

In step 170, and based on information from the virtual 3D image, the dentist or a technician may generate a 3D virtual prosthesis model of a crown to be fitted on a tooth stump or of a bridge to be fitted on the tooth surface, to generate a digital file. Alternatively, the outer surface of the prosthesis may be designed manually if desired. Optionally, and typically, the prosthesis model may also include a virtual model of a coping plus a virtual model of a cap that is to be mounted onto the coping. The coping may be manufactured using any suitable method, for example as disclosed in WO 2004/087000, also assigned to the present Assignee, and the contents of which are incorporated herein in their entirety. The cap or full prosthesis may be manufactured using any suitable method, for example as disclosed in U.S. Ser. No. 11/046,709 or in U.S. Provisional Application No. 60/632,350, also assigned to the present Assignee, and the contents of which are incorporated herein in their entirety.

In the final step, the prosthesis may be installed in the oral cavity of the patient.

In the method claims that follow, alphanumeric characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed exemplary embodiments in accordance with the invention, it will be appreciated that many changes may be made therein without departing from the spirit of the invention.

What is claimed is:

1. A system for manipulating a virtual dental model, the system comprising:
   a hand-held scanner; and
   a computer having instructions that, when executed, cause the system to:
     identify on a 3D virtual model of a dental site, a first 3D virtual model portion comprising data representing an obscuring material over a first portion of a tooth;
     trim the 3D virtual model based on the identified first 3D virtual model portion;
     generate an auxiliary 3D virtual model that includes a representation of the first portion of the tooth representing dental surfaces of the first portion of the tooth; and
     combine the auxiliary 3D virtual model with the trimmed 3D virtual model to create a completed trimmed 3D virtual model including data representative of the dental surfaces of the first portion of the tooth.

2. The system of claim 1, wherein the instructions that, when executed, cause the system to generate the auxiliary 3D virtual model that includes a representation of the first portion of the tooth representing dental surfaces of the first portion of the tooth comprise instructions that cause the system to extrapolate data representing the first portion of the tooth.

3. The system of claim 1, wherein the instructions that, when executed, cause the system to identify on the 3D virtual model of the dental site, the first 3D virtual model portion comprising data representing the obscuring material over the first portion of the tooth comprise instructions that cause the system to identify the first 3D virtual model portion comprising data representing the obscuring material.

4. The system of claim 3, wherein the instructions that, when executed, further cause the system to:
   mark the identified first 3D virtual model portion comprising data representing the obscuring material.

5. The system of claim 4, wherein the instructions that, when executed, cause the system to trim the 3D virtual model to remove the first 3D virtual model portion comprising the data representing the obscuring material cause the system to trim the marked and identified first 3D virtual model portion comprising data representing the obscuring material.

6. The system of claim 3, wherein the instructions that, when executed, cause the system to trim the 3D virtual model to remove the first 3D virtual model portion comprising the data representing the obscuring material cause the system to trim the identified first 3D virtual model portion comprising data representing the obscuring material.

7. The system of claim 1, wherein the first 3D virtual model portion comprises an obscured portion of a finish line.

8. The system of claim 7, wherein the instructions that, when executed, cause the system to combine the auxiliary 3D virtual model with the trimmed 3D virtual model cause the system to create a completed trimmed 3D virtual model including data representative of an unobscured finish line.

9. The system of claim 1, wherein the first 3D virtual model portion comprises an obscured portion of an emerging profile of the tooth.

10. The system of claim 9, wherein the instructions that, when executed, cause the system to combine the auxiliary 3D virtual model with the trimmed 3D virtual model cause the system to create a completed trimmed 3D virtual model including data representative of the emerging profile.

11. A method for manipulating a virtual dental model, the system comprising:
    identifying on a 3D virtual model of a dental site, a first 3D virtual model portion comprising data representing an obscuring material over a first portion of a tooth;
    trimming the 3D virtual model based on the identified first 3D virtual model portion;

generating an auxiliary 3D virtual model that includes a representation of the first portion of the tooth representing dental surfaces of the first portion of the tooth; and combining the auxiliary 3D virtual model with the trimmed 3D virtual model to create a completed trimmed 3D virtual model including data representative of the dental surfaces of the first portion of the tooth.

12. The method of claim 11, generating the auxiliary 3D virtual model that includes a representation of the first portion of the tooth representing dental surfaces of the first portion of the tooth comprises extrapolating data representing the first portion of the tooth.

13. The method of claim 11, where identifying on the 3D virtual model of the dental site, the first 3D virtual model portion comprising data representing the obscuring material over the first portion of the tooth comprises identifying the first 3D virtual model portion comprising data representing the obscuring material.

14. The method of claim 13, further comprising:
marking the identified first 3D virtual model portion comprising data representing the obscuring material.

15. The method of claim 14, wherein the 3D virtual model to remove the first 3D virtual model portion comprising the data representing the obscuring material comprises trimming the marked and identified first 3D virtual model portion comprising data representing the obscuring material.

16. The method of claim 13, wherein trimming the 3D virtual model to remove the first 3D virtual model portion comprising the data representing the obscuring material comprises trimming the identified first 3D virtual model portion comprising data representing the obscuring material.

17. The method of claim 11, wherein the first 3D virtual model portion comprises an obscured portion of a finish line.

18. The method of claim 17, combining the auxiliary 3D virtual model with the trimmed 3D virtual model comprises creating a completed trimmed 3D virtual model including data representative of an unobscured finish line.

19. The method of claim 11, wherein the first 3D virtual model portion comprises an obscured portion of an emerging profile of the tooth.

20. The method of claim 19, combining the auxiliary 3D virtual model with the trimmed 3D virtual model comprises creating a completed trimmed 3D virtual model including data representative of the emerging profile.

* * * * *